(12) United States Patent
Wakamatsu

(10) Patent No.: US 8,176,772 B2
(45) Date of Patent: May 15, 2012

(54) PIEZOELECTRIC SENSOR AND SENSING INSTRUMENT

(75) Inventor: Shunichi Wakamatsu, Sayama (JP)

(73) Assignee: Nihon Dempa Kogyo Co., Ltd., Tokyo (JP)

( * ) Notice: Subject to any disclaimer, the term of this patent is extended or adjusted under 35 U.S.C. 154(b) by 583 days.

(21) Appl. No.: 12/310,377

(22) PCT Filed: Aug. 29, 2007

(86) PCT No.: PCT/JP2007/067243
§ 371 (c)(1),
(2), (4) Date: Feb. 23, 2009

(87) PCT Pub. No.: WO2008/026764
PCT Pub. Date: Mar. 6, 2008

(65) Prior Publication Data
US 2010/0236331 A1    Sep. 23, 2010

(30) Foreign Application Priority Data
Aug. 30, 2006   (JP) .................... 2006-233963

(51) Int. Cl.
*G01N 29/036* (2006.01)
(52) U.S. Cl. ............. 73/61.49; 73/61.75; 73/61.79; 73/64.53; 73/579

(58) Field of Classification Search ............. 73/24.01, 73/24.03, 24.06, 61.45, 61.49, 61.75, 61.79, 73/64.53, 579; 310/311, 323.21, 344
See application file for complete search history.

(56) References Cited

U.S. PATENT DOCUMENTS

| 6,472,798 | B2 * | 10/2002 | Kishimoto | 310/344 |
| 7,055,377 | B2 * | 6/2006 | Paul et al. | 73/54.41 |
| D540,700 | S * | 4/2007 | Wakamatsu | D10/46 |

FOREIGN PATENT DOCUMENTS

| JP | 9-145583 | 6/1997 |
| JP | 11-183479 | 7/1999 |
| JP | 2006-029873 | 2/2006 |
| JP | 2006-194866 | 7/2006 |

* cited by examiner

*Primary Examiner* — Daniel Larkin
(74) *Attorney, Agent, or Firm* — Jordan and Hamburg LLP

(57) ABSTRACT

A piezoelectric sensor senses a substance to be measured in a sample solution, thereby conducting high-precision measurement. A pressing member has a solution storage space with a bottom surface being one surface of a piezoelectric resonator, and covering a recessed portion of a wiring board. The wiring board includes an annular projection surrounding the solution storage space and pressing a surface of the piezoelectric resonator. The wiring board is made of an elastic material. The annular projection has side surfaces that get smaller in diameter toward a lower side. The side surface of the solution storage space makes an obtuse angle to its bottom surface. At a corner portion made by these surfaces, an upper side of the bubbles are opened, and therefore, bubbles, even if entering the solution storage space, can float up.

10 Claims, 15 Drawing Sheets

(a)

(b)

(a)

(b)

PRIOR ART

PIEZOELECTRIC SENSOR AND SENSING INSTRUMENT

TECHNICAL FIELD

The present invention relates to a piezoelectric sensor which includes a piezoelectric resonator having an excitation electrode provided on one surface of a piezoelectric piece to be in contact with a measurement atmosphere and an excitation electrode provided on the other surface to face an airtight space, and which senses a substance to be measured by detecting a change in natural frequency of the piezoelectric resonator, and relates to a sensing instrument using the piezoelectric sensor.

BACKGROUND ART

As a method for sensing the presence/absence of a trace substance, for example, an environmental pollutant such as dioxin or a disease marker such as a hepatitis C virus and C-reactive protein (CRP), in a sample solution, and for measuring the concentration of these substances, there has been widely known a measurement method using: a quartz sensor which includes a piezoelectric resonator, for example, a quartz resonator; and a measuring device which is electrically connected to the quartz sensor and includes an oscillator circuit or the like for oscillating the quartz resonator.

Concretely, in the measurement method, the quartz sensor including the quartz resonator called a Langevin-type or the like which includes: a quartz piece being, for example, a plate-shaped piezoelectric piece; and a pair of foil-shaped electrodes for excitation (excitation electrodes) provided on one surface and the other surface of the quartz piece so as to sandwich the quartz piece is structured such that the electrode on the one surface is in contact with a measurement atmosphere (sample solution) and the electrode on the other surface faces an airtight space, and the method utilizes such a property that when a substance to be measured in the sample solution comes into contact with the electrode on the one surface, the natural frequency of the quartz piece changes according to a mass of the substance which is in contact with the electrode.

The reason why the quartz resonator is structured such that only the one surface thereof is in contact with the measurement atmosphere and the other surface faces the airtight space as described above is because this structure is preferable for stable oscillation of the quartz resonator. Generally, an adsorption layer on whose front surface, for example, an antibody is attached is provided on the electrode on the one surface of the quartz resonator. This antibody selectively adsorbs one of the substances to be measured, for example, described above, by an antigen-antibody reaction, and when the substance to be measured is adsorbed by the adsorption layer, the frequency of the quartz piece changes according to an adsorption amount of the substance to be measured. However, when this measurement method is implemented for research, there is a case where the one surface of the quartz resonator is in contact with the measurement atmosphere without the adsorption layer being provided on the front surface of the quartz resonator, and the antibody is physically made to adhere to the electrode of the quartz resonator for the purpose of, for example, analyzing how the antibody adheres to the substance to be measured.

FIG. 15 shows an example of the structure of the vicinity of the quartz resonator provided in the aforesaid quartz sensor. In the drawing, 11 denotes a wiring board, and the quartz resonator 12 is placed on the wiring board 11. The excitation electrodes, not shown, provided on the front and rear surfaces of the quartz resonator 12 are electrically connected to electrodes provided on the wiring board 11, so that the resonator 12 is electrically connected to the wiring board 11.

In the drawing, 13 denotes a through hole bored in the wiring board 11 in its thickness direction, and in the drawing, 14 denotes a sealing member covering the through hole 13 from a rear surface side of the board 11. A region surrounded by these sealing member 14, through hole 11, and quartz resonator 12 forms an airtight space, and the excitation electrode on the rear surface of the quartz resonator 12 faces the airtight space. In the drawing, 15 denotes a quartz pressing member in a plate shape made of, for example, rubber or the like and it presses the quartz resonator 12 toward the board 11 to fix the position of the quartz resonator 12.

In the drawing, 16 denotes an opening portion provided to penetrate through the quartz pressing member 15 in the thickness direction and it faces the excitation electrode on the front surface of the quartz resonator 12. In the drawing, 17 denotes an annular projection of the quartz pressing member 15, which will be described later. A predetermined amount of the sample solution is stored in a solution storage space 18 surrounded by the opening portion 16 and the annular projection 17, so that the excitation electrode comes into contact with the measurement atmosphere.

In the quartz sensor as described above, a large stress, if applied to the quartz resonator 12 by the quartz pressing member 15, hinders the oscillation of the quartz resonator 12, and the smaller the stress is, the more stably the quartz resonator 12 oscillates to enable higher-precision measurement. Therefore, it has been considered to reduce the stress by decreasing an area of a portion, of the quartz pressing member 15, that is in contact with and presses the quartz resonator 12. As a concrete example of this, it has been considered to form the annular projection 17 on a rear surface of the pressing member 15 so as to surround the periphery of the opening portion 16 as shown in the drawing and press the quartz resonator 12 by a tip portion of the projection 17 toward the wiring board 11 to fix the position of the quartz resonator 12.

However, with such a structure, bubbles 19 are sometime formed from air existing in the solution storage space 18 and air mixed in the sample solution when, for example, the sample solution is supplied to the solution storage space 18. In the solution storage space 18, a pressure is applied toward a corner portion made by an outwardly/downwardly inclined peripheral side surface of the projection 17 and the front surface of the quartz resonator 12 as shown by the arrows in the drawing, and therefore, the bubbles 19 sometimes enter the corner portion. At this time, since the inner peripheral side surface of the projection 17 is above the bubbles 19, this surface may possibly prevent the bubbles 19 from floating up to shut the bubbles 19 in the corner portion. In this case, an amount of the sample solution 18 stored in the solution storage space 18 changes by a volume of the bubbles 19, and being influenced by this, an amount of the substance to be measured in the solution storage space 18 also changes. This is likely to cause a measurement error, and especially because this measurement method is used to sense a trace substance as previously described, such a slight change in the amount of the sample solution may possibly cause an error, for example, a substance that should be able to be detected cannot be detected.

A patent document 1 and a patent document 2 also describe quartz sensors utilizing a Languban-type quartz resonator, but neither of them solves the aforesaid problems.

Patent Document 1: Japanese Patent Application Laid-open No. 2006-029873 (paragraph 0020, paragraph 0021, and FIG. 1)

Patent Document 2: Japanese Patent Application Laid-open No. Hei 11-183479 (FIG. 2)

DISCLOSURE OF THE INVENTION

The present invention was made under the aforesaid circumstances, and an object thereof is to provide a technique for high-precision measurement in a piezoelectric sensor which includes a piezoelectric resonator and senses a substance to be measured in a sample solution based on a change in natural frequency of the piezoelectric resonator, which change is caused when the substance to be measured comes into contact with an excitation electrode on one surface of the piezoelectric resonator, and in a sensing instrument using the piezoelectric sensor.

A piezoelectric sensor of the present invention is a piezoelectric sensor electrically connected to a measuring device main body in order to sense a substance to be measured in a sample solution, the piezoelectric sensor including:

a wiring board which has a connection terminal portion connected to the measuring device main body and on whose one surface an electrode electrically connected to the connection terminal portion and a recessed portion forming an airtight space are provided;

a piezoelectric resonator which includes excitation electrodes provided on one surface and the other surface of a plate-shaped piezoelectric piece respectively and electrically connected to the electrode, and which is provided on the wiring board to cover the recessed portion, with the excitation electrode on the other surface facing the recessed portion;

a pressing member in which a solution storage space having a bottom surface being the one surface of the piezoelectric resonator is formed, and which is made of an elastic material provided to surround the solution storage space; and a solution injection cover placed opposite the wiring board to cover the pressing member, and having, on a front surface thereof, an injection port which communicates with the solution storage space and through which the sample solution is injected to the solution storage space, wherein the pressing member includes an annular projection which presses a portion, of the one surface of the piezoelectric resonator, outside the recessed portion toward the wiring board to fix a position of the piezoelectric resonator;

a tip of the annular projection has an acute angle, with both side surfaces of the annular projection getting smaller in diameter toward a lower side and a distance between the both side surfaces getting smaller toward the lower side; and a natural frequency of the piezoelectric resonator changes when the substance to be measured in the sample solution stored in the solution storage space comes into contact with the one surface of the piezoelectric resonator.

In the piezoelectric sensor, for example, a claw portion bending inward may be provided on an edge portion of the solution injection cover and a cutout portion may be provided in the wiring board, and the solution injection cover may be attached to the wiring board while pressing the pressing member toward the wiring board, by the claw portion catching a peripheral edge portion of the wiring board in the cutout portion owing to an inward restoring force of the claw portion.

A piezoelectric sensor of another invention is a piezoelectric sensor electrically connected to a measuring device main body in order to sense a substance to be measured in a sample solution, the piezoelectric sensor including:

a wiring board which has a connection terminal portion connected to the measuring device main body and on whose one surface an electrode electrically connected to the connection terminal portion and a recessed portion forming an airtight space are provided;

a piezoelectric resonator which includes excitation electrodes provided on one surface and the other surface of a plate-shaped piezoelectric piece respectively and electrically connected to the electrode, and which is provided on the wiring board to cover the recessed portion, with the excitation electrode on the other surface facing the recessed portion;

a pressing member in which a solution storage space having a bottom surface being the one surface of the piezoelectric resonator is formed, and which is made of an elastic material provided to surround the solution storage space;

a support supporting the wiring board; and a solution supply/discharge cover which includes: a supply channel communicating with the solution storage space to supply the sample solution to the solution storage space; and a discharge channel communicating with the solution storage space to discharge the sample solution stored in the space, and which is fixed to the support while placed opposite the wiring board to cover the pressing member, wherein the pressing member includes an annular projection which presses a portion, of the one surface of the piezoelectric resonator, outside the recessed portion toward the wiring board to fix a position of the piezoelectric resonator;

a tip of the annular projection has an acute angle, with both side surfaces of the annular projection getting smaller in diameter toward a lower side and a distance between the both side surfaces getting smaller toward the lower side; and a natural frequency of the piezoelectric resonator changes when a liquid flow is formed in the solution storage space by the supply and discharge of the sample solution to bring the substance to be measured in the sample solution into contact with the one surface of the piezoelectric resonator.

In the piezoelectric sensor, for example, a projection entering the solution storage space to restrict the liquid flow in an up and down direction in the solution storage space may be provided in a lower portion of the solution supply/discharge cover, and further, for example, holes overlapping each other may be provided in the wiring board and the pressing member respectively, and a projection corresponding to the holes may be provided in the support to fix positions of the wiring board and the pressing member on the support.

Further, for example, the injection channel includes a solution supply pipe attachable/detachable to/from the solution supply/discharge cover, the discharge channel includes a solution discharge pipe attachable/detachable to/from the solution supply/discharge cover, and the solution supply pipe and the solution discharge pipe are mounted to the solution supply/discharge cover via connectors attachable/detachable to/from the solution supply/discharge cover.

Further, in these piezoelectric sensors, for example, the excitation electrodes of the piezoelectric resonator and the electrode of the wiring board are electrically connected to each other by the annular projection pressing the piezoelectric resonator toward the wiring board.

A sensing instrument of the present invention includes: the above-described piezoelectric sensor; and a measuring device main body detecting a change amount of the natural frequency of the piezoelectric resonator to sense the substance to be measured in the sample solution based on the detection result.

The piezoelectric sensor of the present invention includes the pressing member in which the solution storage space having the bottom surface being the one surface of the piezoelectric resonator provided to cover the recessed portion of the wiring board is formed, which includes the annular projection provided to surround the solution storage space and pressing the portion, of the one surface of the piezoelectric resonator, outside the recessed portion toward the wiring board to fix the position of the piezoelectric resonator, and which is made of the elastic material, and the annular projection is structured such that the both side surfaces thereof get smaller in diameter toward the lower side and the distance between the both side surfaces gets smaller toward the lower side. With such a structure, since a pressure applied to the piezoelectric resonator is reduced owing to a reduced area of the portion, of the pressing member, that is in contact with the piezoelectric resonator, a hindrance to the oscillation of the piezoelectric resonator is reduced, and moreover, even if bubbles enter the solution storage space at the time of the supply of the sample solution to the solution storage space, since the side surface of the solution storage space makes an obtuse angle to its bottom surface and in the corner portion made by these surfaces, the upper side of the bubbles is opened, the bubbles can float up to move toward the outside of the solution storage space and thus are prevented from staying in the space, and therefore, an amount of the sample solution stored in the solution storage space is prevented from decreasing by a volume of the bubbles. As a result, high-precision measurement is made possible.

Further, according to the piezoelectric sensor of the other invention, similarly to the piezoelectric sensor of the present invention, it is also possible to prevent an amount of the sample solution stored in the solution storage space from changing, which enables high-precision measurement.

BEST MODE FOR CARRYING OUT THE INVENTION

Figure 1:
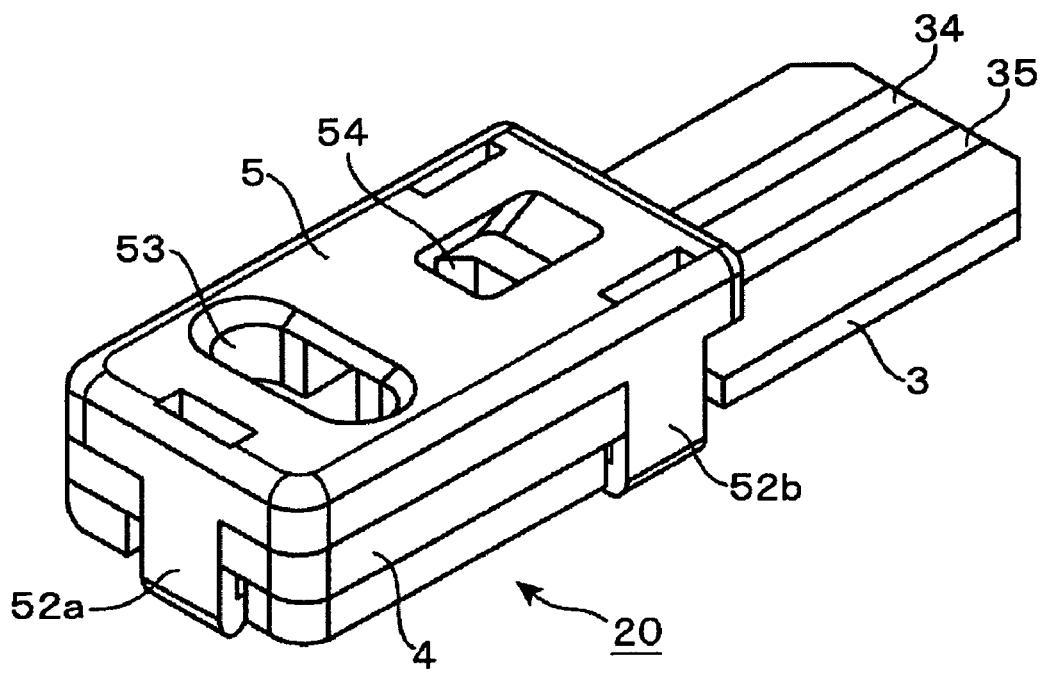
FIG. 1 is a perspective view of a quartz sensor according to an embodiment of the present invention.
Figure 2:
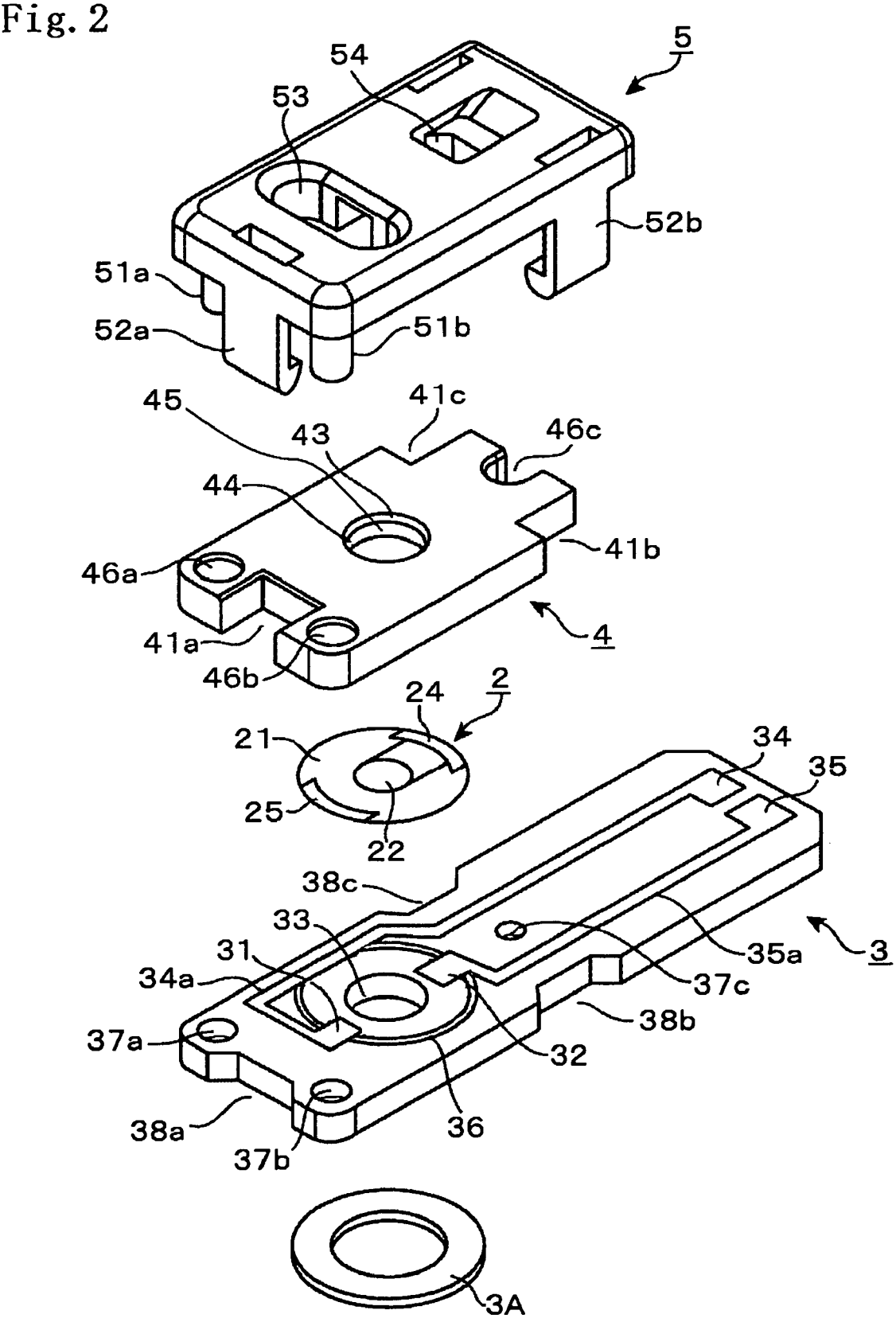
FIG. 2 is an exploded perspective view of the quartz sensor.
Figure 3:
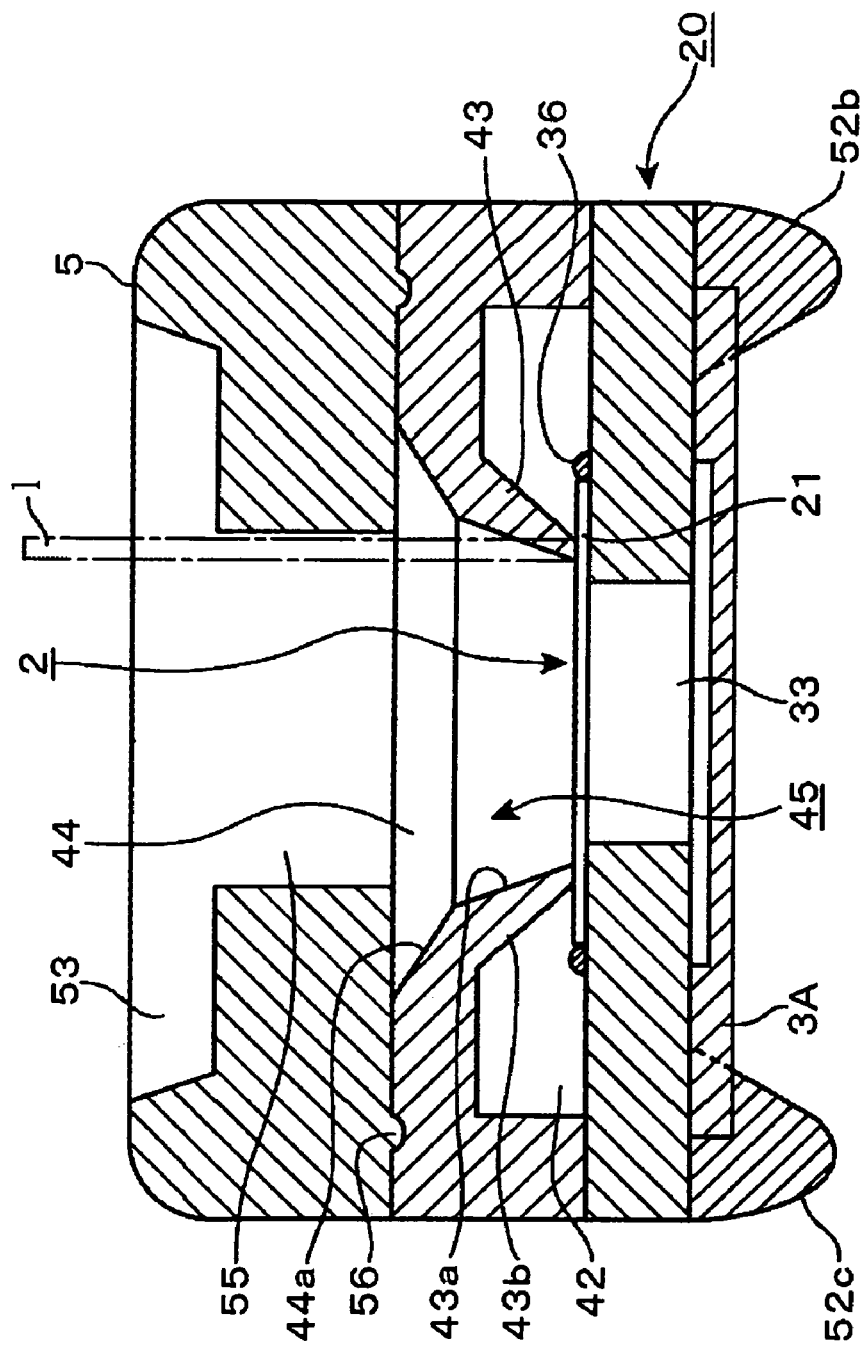
FIG. 3 is a vertical front sectional view of the quartz sensor.
Figure 4:
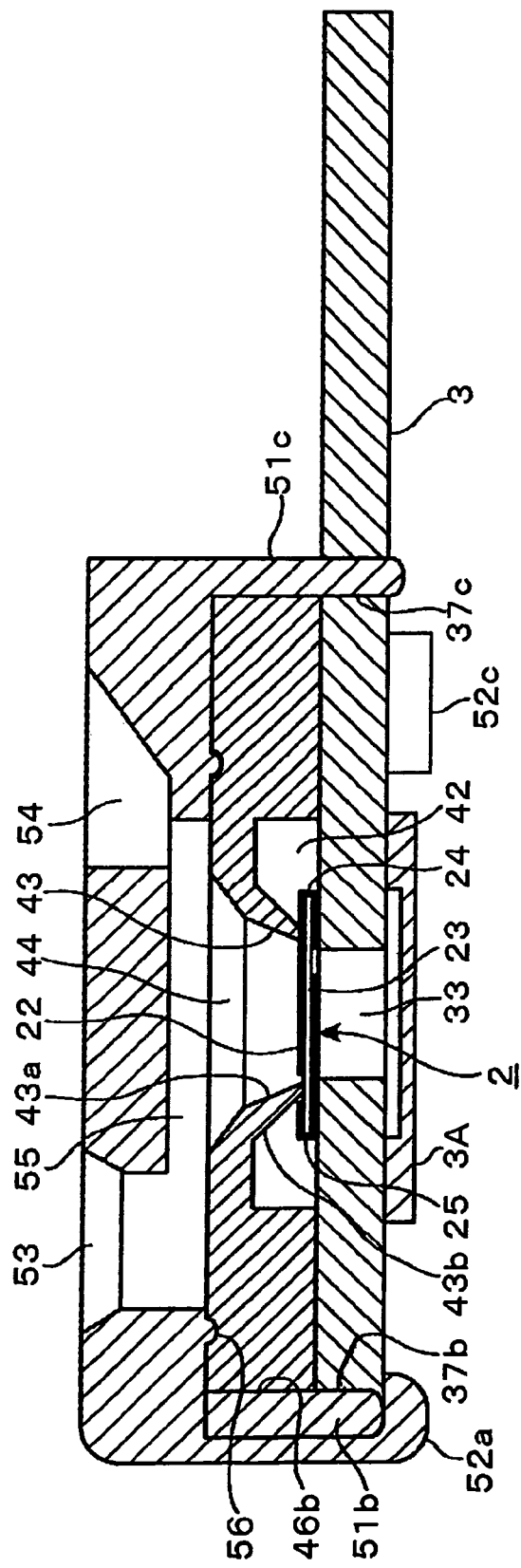
FIG. 4 is a vertical side sectional view of the quartz sensor.

A first embodiment of a quartz sensor as an example of a piezoelectric sensor according to the present invention will be described by using FIG. 1 to FIG. 4. FIG. 1 is a perspective view showing a quartz sensor 20 as an example of the piezoelectric sensor according to the present invention. FIG. 2 is an exploded perspective view showing upper surface sides of respective components of the quartz sensor 20, and as shown in FIG. 2, the quartz sensor 20 includes a sealing member 3A, a wiring board 3, a quartz resonator 2 as a piezoelectric resonator, a quartz pressing member 4, and a solution injection cover 5, and these components are stacked in this order from the bottom. FIG. 3 and FIG. 4 are a vertical front sectional view and a vertical side sectional view of the quartz sensor 20 respectively.

The quartz resonator 2 includes a quartz piece 21 as a piezoelectric piece, excitation electrodes 22, 23, and leading electrodes 24, 25. The quartz piece 21 has an equivalent thickness of, for example, 1 $\mu$m to 300 $\mu$m, preferably, 185 $\mu$m, and is formed in a plate shape with part of its circumference linearly cut. The excitation electrode 22 and the other excitation electrode 23 having a foil shape are bonded to one surface and the other surface of the quartz piece 21 respectively and are formed having a circular shape smaller in diameter than the quartz piece 21. Further, the leading electrode 24 having a foil shape is formed so that one end thereof is connected to the excitation electrode 22 on the one surface of the quartz piece 21, and this leading electrode 24 is bent along an end surface of the quartz piece 21 and is bent toward the other surface side of the quartz piece 21.

Further, the other leading electrode 25 having a foil shape is formed so that one end thereof is connected to the other excitation electrode 22 on the other surface of the quartz piece 21, in the same layout as that of the aforesaid leading electrode 24, and thus on both surfaces of the quartz piece 21, the excitation electrode 22 (23) and the leading electrode 24 (25) are arranged in the same layout.

The equivalent thickness of the excitation electrodes 22, 23 and the leading electrodes 24, 25 is, for example, 0.2 $\mu$m, and as a material of the electrodes, gold is used, for instance. Note that in FIG. 3, the electrodes of the quartz resonator 2 are not shown for convenience sake. Further, as will be described later, the excitation electrode 22 is provided so as to face a solution storage space 45 to which a sample solution is supplied, and therefore, a not-shown adsorption layer on whose front surface an antibody is attached is provided on the excitation electrode 22. This antibody selectively adsorbs a substance to be measured, for example, dioxin by an antigen-antibody reaction, and when the substance to be measured is adsorbed by the adsorption layer, the frequency of the quartz piece 21 changes according to an adsorption amount of the substance to be measured.

Next, the wiring board 3 will be described. The wiring board 3 is formed by, for example, a printed circuit board, and an electrode 31 and an electrode 32 are provided to be apart from each other in a direction from a front end side toward a back end side of a front surface of the wiring board 3. Between the electrodes 31, 32, a through hole 33 bored in a thickness direction of the wiring board 3 is formed so as to be apart from the electrodes 31, 32. As will be described later, the through hole 33 forms a recessed portion as an airtight space faced by the excitation electrode 23 on the rear surface of the quartz resonator 2, and is formed to have a diameter large enough to house the excitation electrode 23.

Further, at positions closer to the back end side than a place where the electrode 32 is formed, two parallel line-shaped conductive path patterns are formed as connection terminal portions 34, 35. The connection terminal portion 34 is electrically connected to the electrode 31 via a pattern 34a, and the other connection terminal portion 35 is electrically connected to the electrode 32 via a pattern 35a. Note that the electrodes and patterns on the board 3 are not shown in FIG. 3 and FIG. 4 for convenience sake.

In the drawings, 36 denotes a weir formed by, for example, photolithography using a resist, and it is formed along an outer contour of the quartz resonator 2. Alternatively, the weir 36 may be formed by, for example, serigraphy. The weir 36 serves to fix the position of the quartz resonator 2, and the quartz resonator 2 is placed on a region surrounded by the weir 36. In the drawings, 37a, 37b, 37c denote engagement holes, which are bored in the thickness direction of the wiring board 3. These engagement holes 37a, 37b, 37c are respectively engaged with engagement projections 51a, 51b, 51c provided on a lower surface of the cover 5. Further, in the drawings, 38a, 38b, 38c are cutout portions formed in a peripheral edge portion of the wiring board 3. Further, claw portions 52a, 52b, 52c bending inward are provided on a peripheral edge portion of the lower surface of the cover 5, and the cutout portions 38a, 38b, 38c are engaged with the claw portions 52a, 52b, 52c respectively.

The sealing member 3A is a film member and together with the through hole 33, it forms the recessed portion as the airtight space.

Next, the quartz pressing member 4 will be described. The quartz pressing member 4 is made of, for example, silicone rubber, and is formed in a shape corresponding to the wiring board 3. Concretely, the quartz pressing member 4 has a plate shape including rectangular cutout portions 41a, 41b, 41c corresponding to the cutout portions 38a, 38b, 38c respectively. The cutout portions 41b, 41c are formed at adjacent corner portions of the quartz pressing member 4. Further, the cutout portion 41a is formed at a center of one front-side edge of the quartz pressing member 4, assuming that the side where the cutout portions 41b, 41c are formed is defined as a back side.

Figure 5:
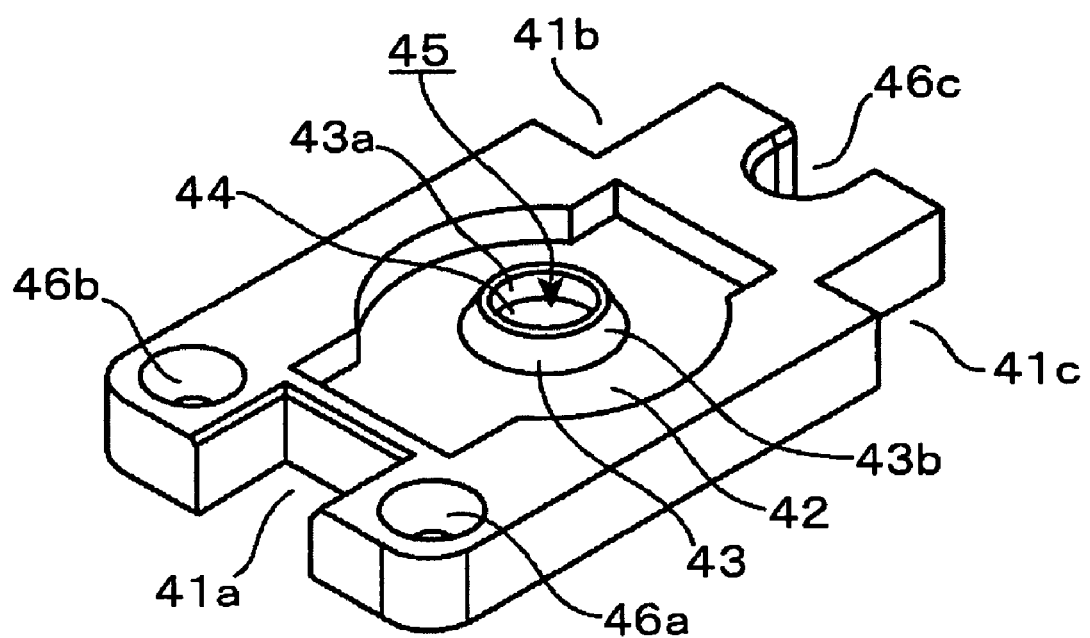
FIG. 5 is a perspective view of a rear surface side of a quartz pressing member included in the quartz sensor.

FIG. 5 is a perspective view showing a lower surface side of the quartz pressing member 4, and the structure of the pressing member 4 will be described with reference to this drawing as well. As shown in FIG. 3, FIG. 4, and FIG. 5, in the lower surface of the pressing member 4, a recessed portion 42 housing the quartz resonator 2 is formed. At a center of a ceiling surface portion (a bottom surface portion if the description is based on the direction in FIG. 5) of the recessed portion 42, an annular projection 43 slightly larger than the through hole 33 in the upper surface of the wiring board 3 is formed. The annular projection 43 serves to press the quartz resonator 2 toward a region surrounding the through hole 33 to fix the position of the quartz resonator 2. Further, as shown in FIG. 2, FIG. 3, and FIG. 4, in a front surface of the quartz pressing member 4, an opening portion 44 is formed, and the opening portion 44 communicates with a space surrounded by the annular projection 43.

A peripheral side surface 44a of the opening portion 44 and an inner peripheral side surface 43a of the annular projection 43 are inclined inward/downward. That is, the opening portion 44 and the annular projection 43 get smaller in diameter toward the lower side. A region surrounded by the peripheral side surfaces 43a, 44a and the quartz resonator 2 forms the solution storage space 45 storing the sample solution.

Further, an outer peripheral side surface 43b of the annular projection 43 is also formed so as to be inclined inward/downward, and a width of the annular projection 43 (distance between the peripheral side surfaces 43a, 43b) gets smaller toward the lower side and its tip has an acute angle. That the tip of the annular projection has an acute angle means here that a contact portion between the quartz resonator and the angular projection (a size of a width 1 shown in FIG. 3) is 0.2 μm to 0.4 μm.

Further, in the drawings, 46a, 46b are engagement holes bored so as to penetrate through the pressing member 4 in the thickness direction, and they are formed so as to correspond to the engagement holes 37a, 37b of the wiring board 3 and the engagement projections 51a, 51b of the solution injection cover 5. In the drawings, 46c denotes an arc-shaped cutout portion formed at a center of a back-side edge, and it corresponds to the engagement hole 37c of the wiring board 3 and the engagement projection 51c of the solution injection cover 5.

Next, the structure of the solution injection cover 5 will be described. The cover 5 is made of, for example, polycarbonate, and at a front side and a back side on its upper surface, an injection port 53 and a check port 54 for the sample solution are formed respectively. As shown in FIG. 4, in the lower surface of the cover 5, an injection channel 55 which is a groove is formed along a longitudinal direction of the cover 5, and one end and the other end of the injection channel 55 are connected to the injection port 53 and the check port 54 respectively. As shown in FIG. 3, the injection channel 55 is provided so as to face the opening portion 44, and the sample solution injected to the injection port 53 is supplied to the solution storage space 45 via the injection channel 55. Further, when a predetermined amount of the sample solution is supplied to the quartz sensor 20, a surface of the sample solution appears in the check port 52, so that the supply of the solution to the sensor 20 can be confirmed.

On the lower surface of the cover 5, an annular weir 56 surrounding the injection channel 55 is provided, and the weir 56 penetrates into the quartz pressing member 4 to serve to prevent the sample solution injected into the injection port 51 from leaking from a gap between the solution injection cover 5 and the pressing member 4.

The above-described quartz sensor 20 is assembled in the following manner. First, the through hole 33 of the wiring board 3 is covered by the sealing member 3A to form the recessed portion in the board 3. Next, the quartz resonator 2 is placed on the wiring board 3 so that the leading electrodes 24, 25 of the quartz resonator 2 overlap the electrodes 31, 32 of the wiring board 3 and the excitation electrode 23 on the rear surface of the quartz resonator 2 overlaps the recessed portion.

Next, after the solution injection cover 5 and the pressing member 4 are stacked on each other by engaging the engagement projections 51a to 51c of the solution injection cover 5 with the engagement holes 46a, 46b and the cutout portion 46c of the quartz pressing member 4, they are stacked on the wiring board 3 so that the claw portions 52a, 52b, 52c of the solution injection cover 5 and the cutout portions 38a, 38b, 38c of the wiring board 3 are fit to each other, and are pressed toward the wiring board 3. Consequently, the claw portions 52a to 52c of the solution injection cover 5 bend toward an outer side of the wiring board 3, and as soon as the claw portions 52a to 52c further reach the lower surface of the peripheral edge portion of the wiring board 3 via the cutout portions 38a to 38c, the claw portions 52a to 52c return to the original shape owing to its inward restoring force, and when the wiring board 3 is sandwiched by the claw portions 52a to 52c to be caught thereby, the pressing member 4 sandwiched between the wiring board 3 and the cover 5 is pressed by them.

Due to elasticity of the pressed pressing member 4, the annular projection 43 presses a portion, of the front surface of the quartz resonator 2, outside the recessed portion, so that the position of the quartz resonator 2 is fixed, a peripheral edge portion thereof comes into close contact with the wiring board 3 to turn the recessed portion formed by the through hole 33 and the sealing member 3A into an airtight space, the excitation electrode 23 on the rear surface of the quartz resonator 2 faces the airtight space, and the leading electrodes 24, 25 of the quartz resonator 2 come into close contact with the electrodes 31, 32 of the wiring board 3 to electrically connect the quartz resonator 2 and the wiring board 3 to each other.

Further, in order to prevent the adhesion of impurities which enter the quartz resonator 2 from the injection port 53 and the check port 54 before the measurement, the injection port 53 and the check port 54 are covered by protection sheets in a film form.

When the quartz sensor 20 in this embodiment is used, an operator injects the sample solution 101 into the injection port 53 of the solution injection cover 5 by using, for example, an injector. The sample solution 101 injected into the injection port 53 is supplied to the solution storage space 45 for the sample solution formed by the opening portion 44 and the annular projection 43, and the excitation electrode 22 on the front surface of the quartz resonator 2 comes into contact with the sample solution 101.

Figure 6:
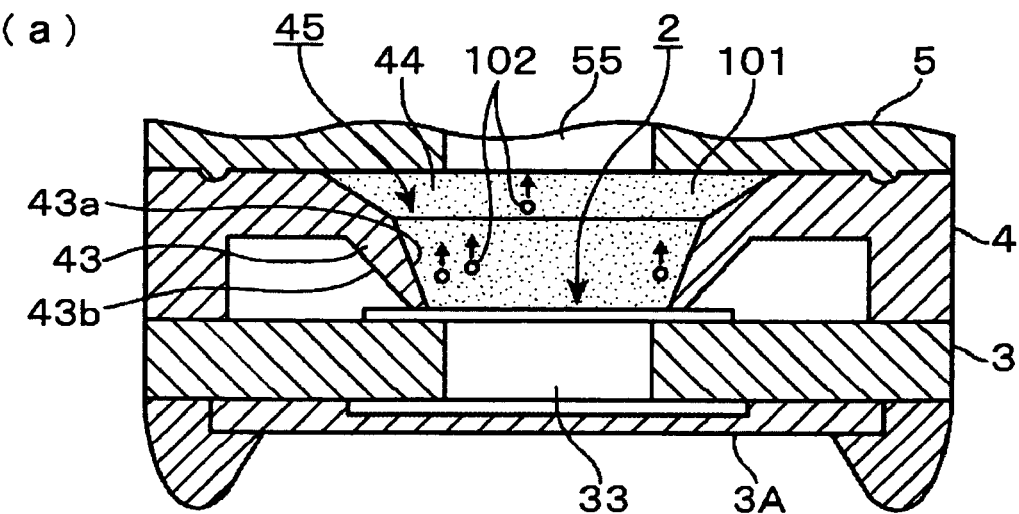
FIG. 6 are explanatory views showing states of bubbles in a sample solution stored in the quartz sensor.
Figure 6:
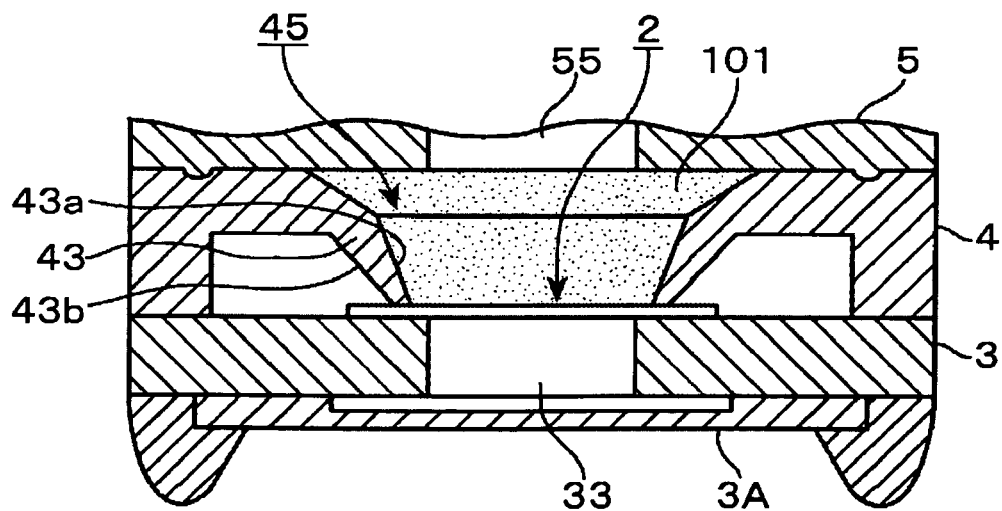

Even if bubbles 102 are formed in the solution storage space 45 at this time, the bubbles 102 move upward in the solution storage space 45 as shown in FIG. 6(*a*), and since there is no obstacle above the bubbles 102, the bubbles 102 can get out of the solution storage space 45 as shown in FIG. 6(*b*), so that the solution storage space 45 is filled with the sample solution 101.

The above-described quartz sensor 20 includes the quartz pressing member 4 in which the opening portion 44 having the inner peripheral side surface 44*a* inclined inward/downward and the solution storage space 45 having the bottom surface being the one side surface of the quartz resonator 2 provided to cover the recessed portion of the wiring board 3 are formed, which includes the annular projection 43 surrounding the solution storage space 45 and pressing the portion, of the one surface of the quartz resonator 2, outside the recessed portion toward the wiring board 3 to fix the position of the quartz resonator 2, and which is made of rubber, and the annular projection 43 is structured such that the inner peripheral side surface 43*a* and the outer peripheral side surface 43*b* thereof both get smaller in diameter toward the lower side and the distance between the both side surfaces gets smaller toward the lower side. With such a structure, since a pressure applied to the quartz resonator 2 is reduced owing to a reduced area of the portion, of the quartz pressing member 4, that is in contact with the quartz resonator 2, a hindrance to the oscillation of the quartz resonator 2 is reduced, and moreover, even if bubbles enter the solution storage space 45 at the time of the supply of the sample solution into the solution storage space 45, since the peripheral side surfaces 43*a*, 44*a* of the solution storage space 45 make obtuse angles to its bottom surface which is the front surface of the quartz resonator 2 and in the corner portion made by these surfaces, the upper side of the bubbles are opened, the bubbles can float up to move toward the outside of the solution storage space and thus are prevented from staying in the space, and therefore, an amount of the sample solution stored in the solution storage space is prevented from decreasing by a volume of the bubbles. As a result, high-precision measurement is made possible.

Further, in the above-described quartz sensor 20, since the annular projection 43 fixes the position of the quartz resonator 2, the electrodes 31, 32 of the wiring board 3 and the electrodes 24, 25 of the quartz resonator 2 are brought into close contact to be electrically connected with each other, which eliminates a need for using, for example, a conductive adhesive or the like for the electrical connection, realizing to simplify manufacturing processes.

Figure 7:
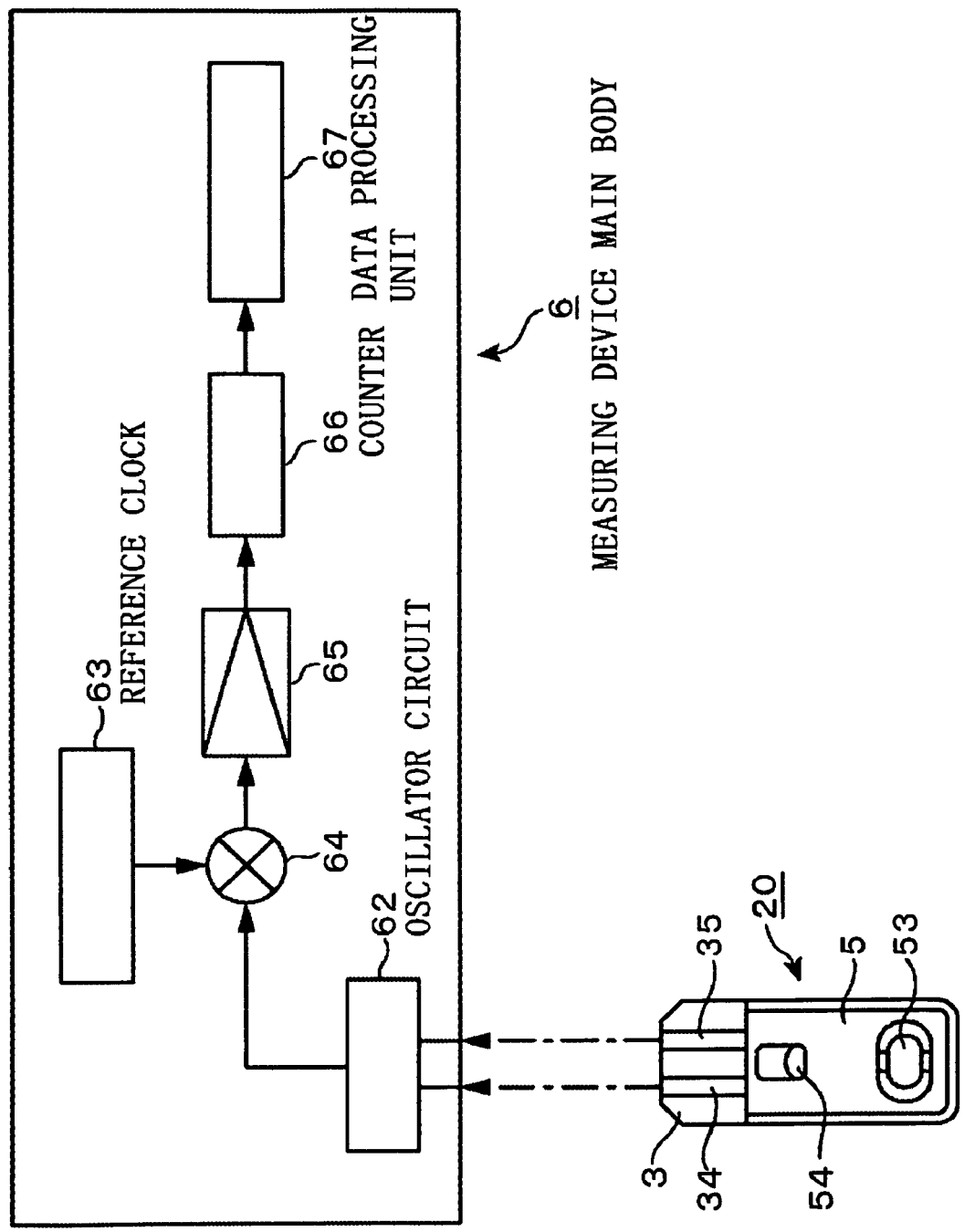
FIG. 7 is a block diagram of a sensing instrument including the quartz sensor.

The above-described quartz sensor 20 is used as a sensing unit of a sensing instrument when connected to a measuring device main body 6 having, for example, the structure shown in FIG. 7 which is a block diagram. In the drawing, 62 denotes an oscillator circuit oscillating the quartz piece 21 of the quartz sensor 20, 63 denotes a reference clock generating unit generating a reference frequency signal, and 64 denotes a frequency difference detector formed by, for example, a heterodyne detector, which, based on a frequency signal from the oscillator circuit 62 and a clock signal from the reference clock generating unit 63, extracts a frequency signal corresponding to a frequency difference therebetween. 65 denotes an amplifying unit, 66 denotes a counter counting a frequency of an output signal from the amplifying unit 65, and 67 denotes a data processing unit. As the frequency of the quartz sensor 20, 9 MHz is selected, for instance, and as the frequency of the reference clock generating unit 63, 10 MHz is selected, for instance. When a substance to be measured, for example, dioxin is not adsorbed by the aforesaid adsorption layer provided on the quartz resonator 2 of the quartz sensor 20, the frequency difference detector 64 outputs a frequency signal (frequency difference signal) corresponding to 1 MHz which is a difference between the frequency from the quartz sensor side and the frequency of the reference clock, but when the substance to be measured contained in the sample solution is adsorbed by the adsorption layer of the quartz resonator 2, the natural frequency of the quartz resonator 2 changes, causing a change in the frequency difference signal, and thus a change in a counter value in the counter 66, whereby the concentration of the substance to be measured or the presence/absence of this substance can be detected.

Figure 8:
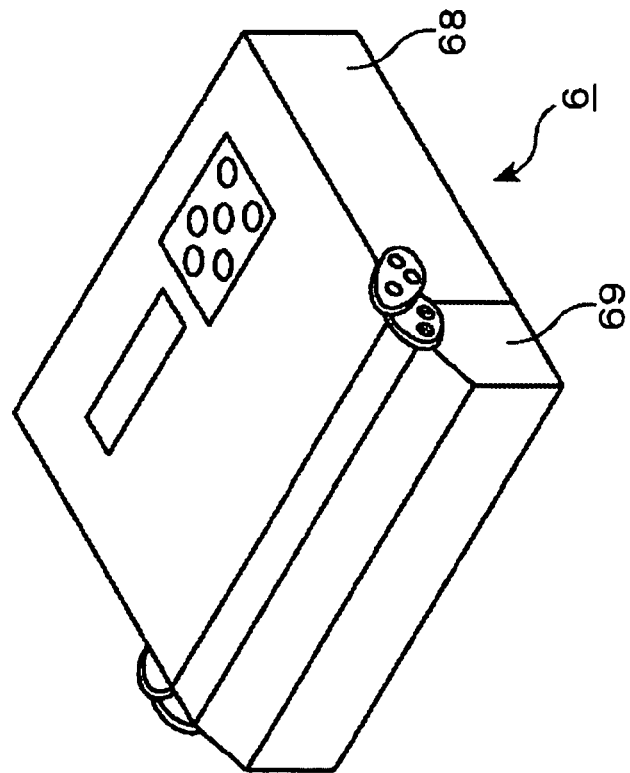
FIG. 8 are perspective views of the sensing instrument.
Figure 8:
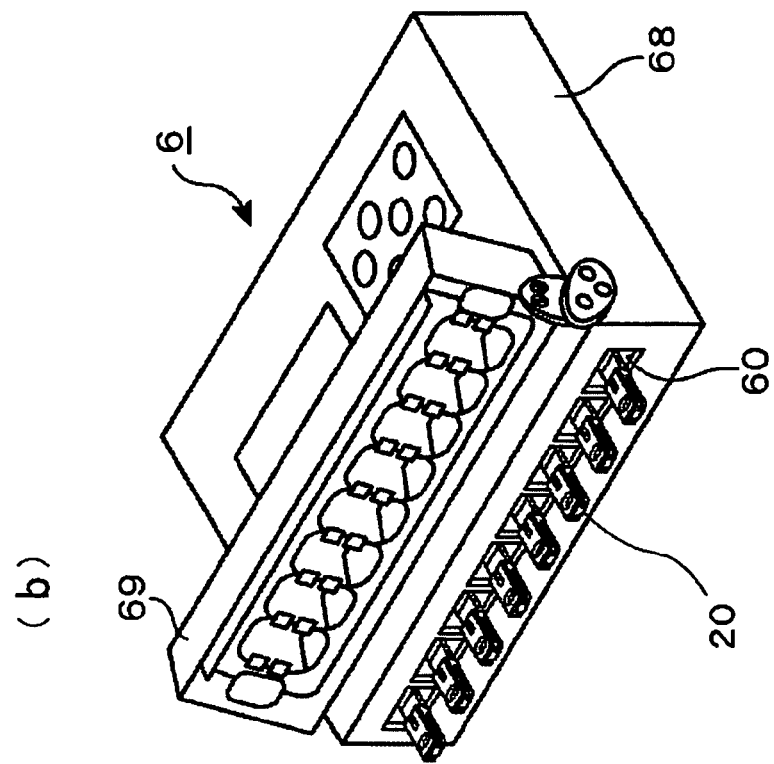

FIGS. 8*a* to 8*b* are views showing an example of the aforesaid measuring device main body 6. As shown in FIG. 8(*a*), the measuring device main body 6 includes a main body portion 68 and an openable/closable cover portion 69 formed on a front surface of the main body portion 68. When the cover portion 69 is opened, the front surface of the main body portion 68 appears as shown in FIG. 8(*b*). On the front surface of the main body portion 68, a plurality of insertion ports 60 for the quartz sensors are formed, and for example, eight insertion holes are arranged in line at equal intervals.

When the back end sides of the wiring boards 3 of the quartz sensors 20 are horizontally inserted up to a prescribed depth of the insertion ports 60 of the measuring device main body 6 respectively, the connection terminal portions 34, 35 of the boards 3 and electrodes formed in the insertion ports 60 are electrically connected and at the same time, the inner parts of the insertion ports 60 hold the wiring boards 3, so that the quartz sensors 20 are fixed to the sensing device main body 6 while kept horizontal.

Incidentally, the quartz pressing member 4 in the above-described quartz sensor 20 may be made of an elastic material other than rubber.

Figure 9:
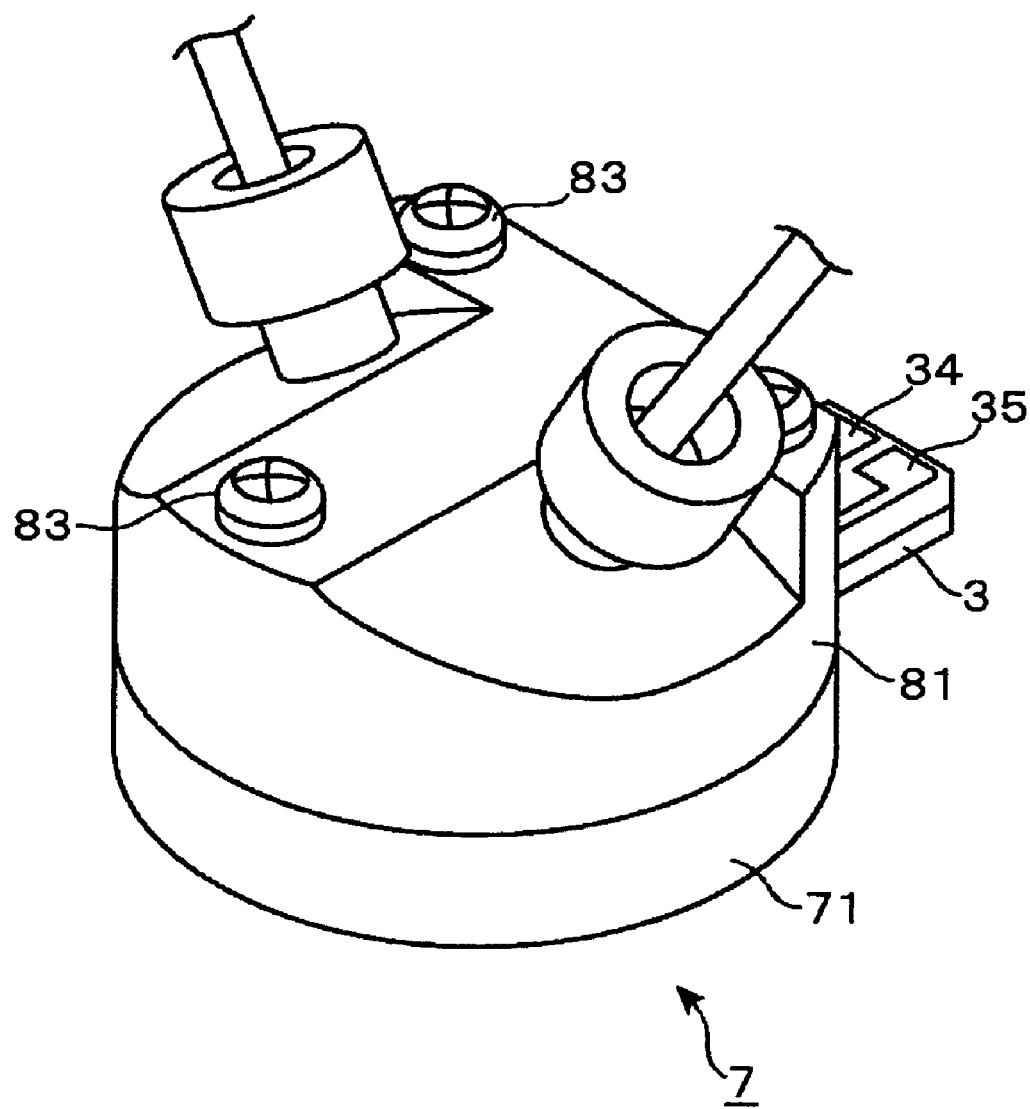
FIG. 9 is a perspective view of a quartz sensor according to another embodiment of the present invention.
Figure 10:
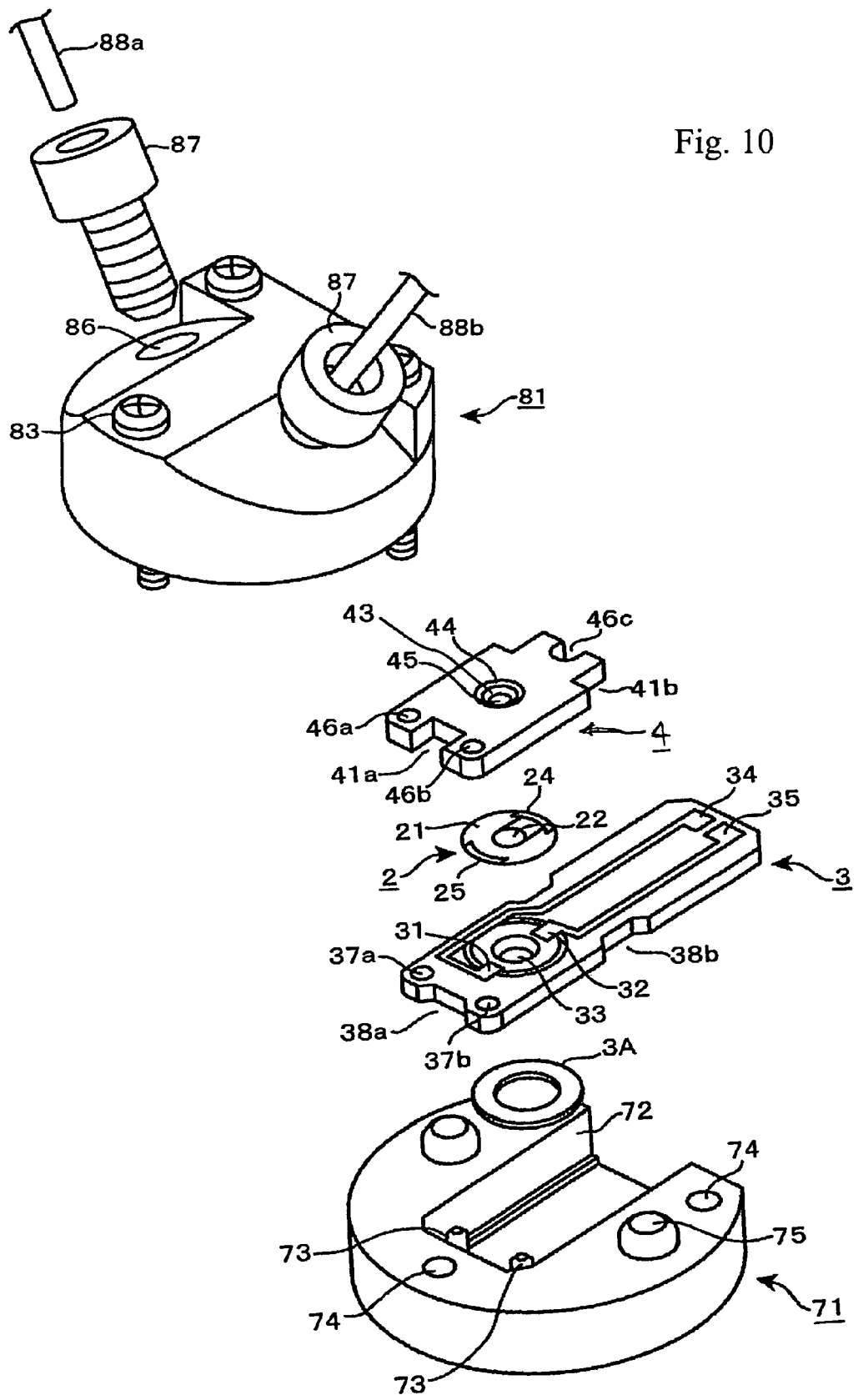
FIG. 10 is an exploded perspective view of the quartz sensor.
Figure 11:
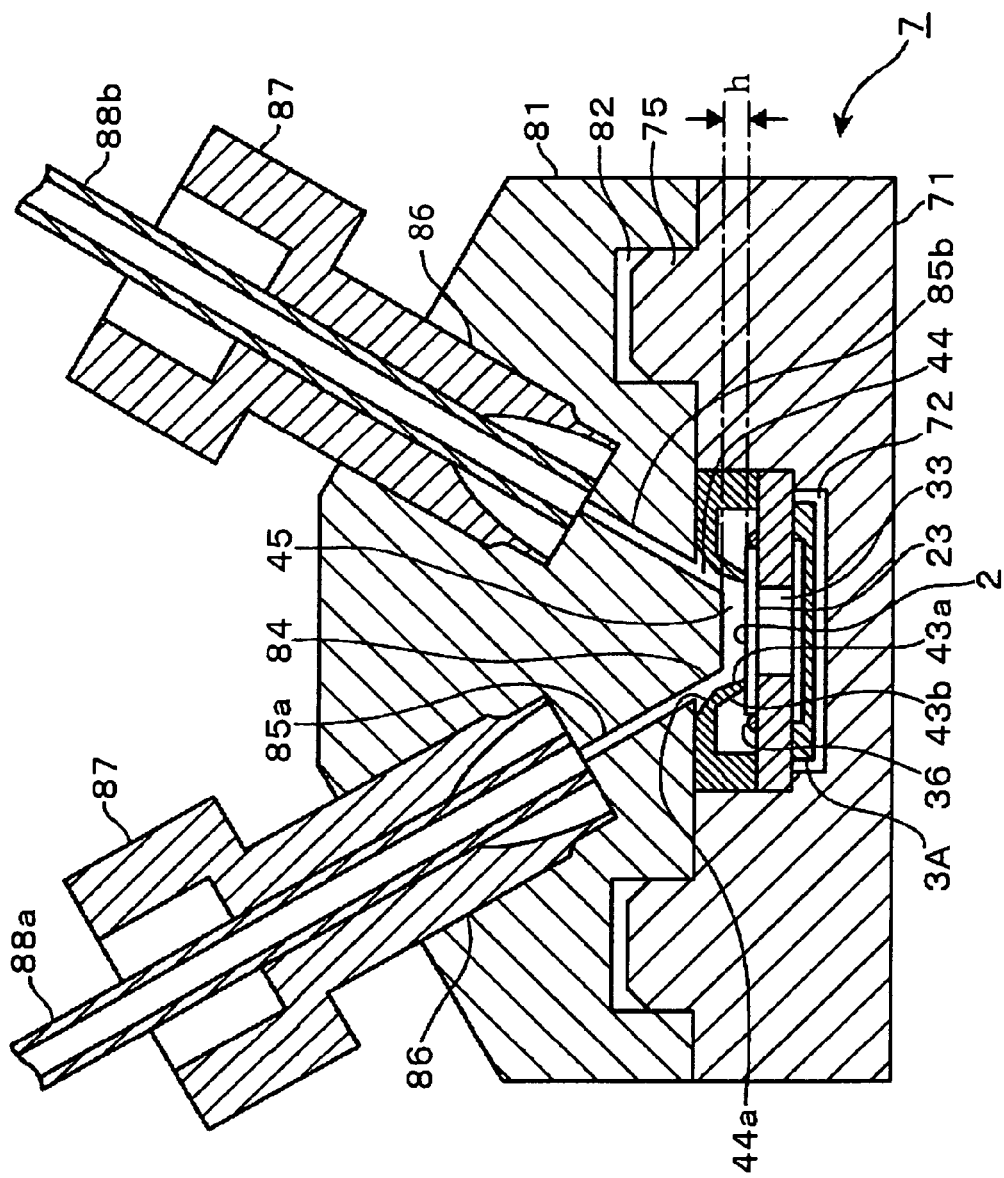
FIG. 11 is a vertical side sectional view of the quartz sensor.

As an example of a quartz sensor according to another embodiment, a quartz sensor 7 will be described below. FIG. 9 is a perspective view of the quartz sensor 7, and FIG. 10 is an exploded perspective view showing upper surface sides of respective members forming the quartz sensor 7. Further, FIG. 11 is a vertical side sectional view of the quartz sensor 7. In FIG. 11, electrodes of a quartz resonator 2 are not shown for convenience sake. In the drawings, 71 denotes a support, in whose front surface a recessed portion 72 housing and holding a wiring board 3 is provided. In the drawings, 73 denotes engagement projections provided in the recessed portion 72. The engagement projections 73 are engaged with engagement holes 37a, 37b of the wiring board 3 and engagement holes 46a, 46b of a quartz pressing member 4 and are provided in order to fix the positions of the wiring board 3 and the quartz pressing member 4. In the drawings, 74 denotes holes whose peripheral side surfaces are threaded.

In the drawings, 81 denotes a solution supply/discharge cover. As shown in FIG. 11, in a lower surface thereof, recessed portions 82 are provided, and when the recessed portions 82 are fit to projections 75 provided on the support 71, the solution supply/discharge cover 81 is positioned relative to the support 71 and is fixed by screws 83 corresponding to the holes 74. The solution supply/discharge cover 81 thus fixed to the support 71 presses the quartz pressing member 4 toward the wiring board 3 housed in the recessed portion 82, so that an annular projection 43 presses the quartz resonator 2 toward the wiring board 3 to fix the position of the quartz resonator 2.

Further, as shown in FIG. 11, on the lower surface of the solution supply/discharge cover 81, a projection 84 corresponding to an opening portion 44 of the pressing member 4 is provided, and in the state where the cover 81 is fixed to the support 71 as described above, the projection 84 enters the opening portion 44. As will be described later, the projection 84 serves to restrict the liquid flow of a sample solution in an up and down direction when the sample solution is supplied to a solution storage space 45, and a distance h between a tip of the projection 84 and an excitation electrode 22 on a front surface of the resonator 2 is, for example, about 0.2 mm to 0.7 μm.

Figure 12:
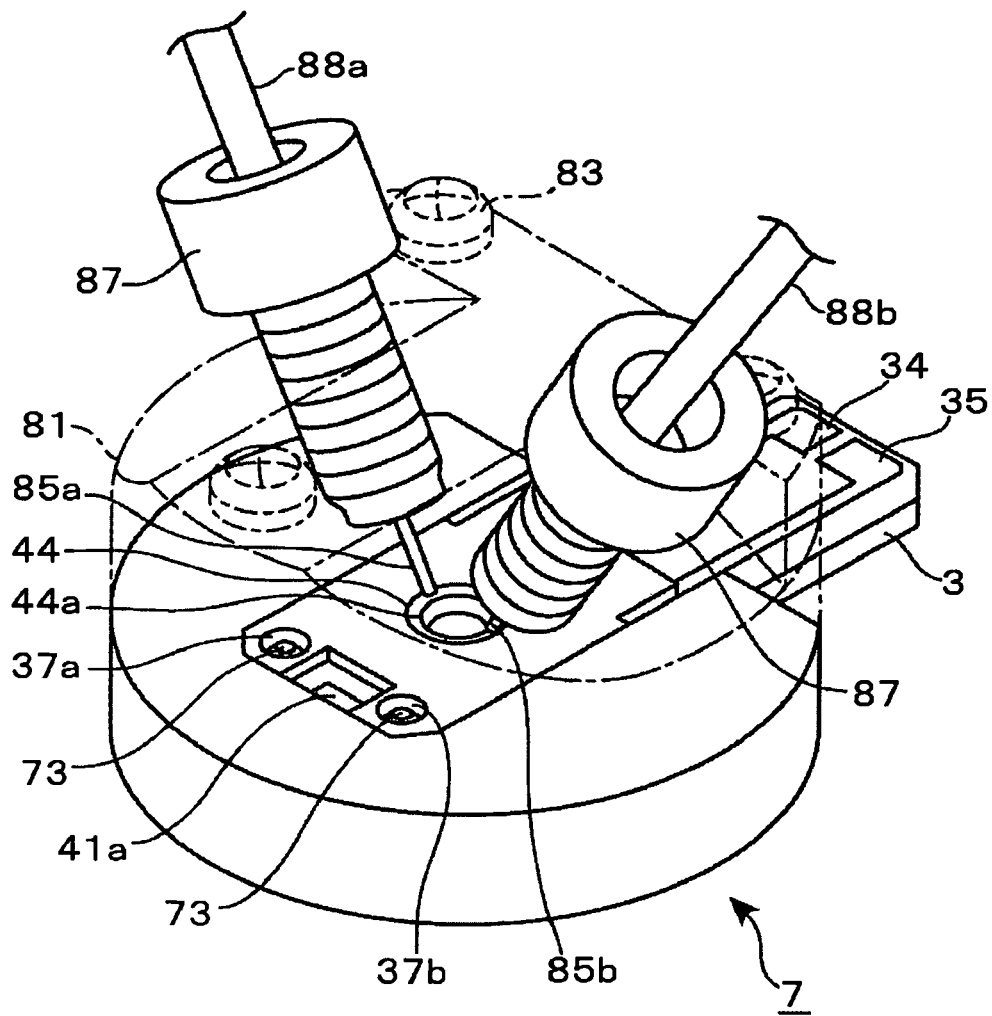
FIG. 12 is a perspective view showing the structure of the inside of a solution supply/discharge cover included in the quartz sensor.

Further, as shown in FIGS. 11 and 12, a channel 85a and a channel 85b for the sample solution are obliquely formed in the solution supply/discharge cover 81 so as to communicate with the solution storage space 45. Further, recessed portions 86, 86 are provided in the solution supply/discharge cover 81, and the recessed portions 86, 86 have peripheral side surfaces which are threaded and bottom surfaces to which openings of one-side ends of the channel 85a and the channel 85b are connected. In the drawings, 87, 87 denote cylindrical connectors, which have threaded outer peripheries so as to correspond to the threads of the recessed portions 86, and which are formed so as to be attachable/detachable to/from the solution supply/discharge cover 81.

In the drawings, 88a, 88b denote a sample solution supply pipe and a sample solution discharge pipe respectively, which are attachable/detachable to/from the connectors 87, and the sample solution supply pipe 88a and the sample solution discharge pipe 88b are obliquely supported by inner walls of the connectors 87 and communicate with the channel 85a and the channel 85b respectively. It should be noted that the solution supply pipe 88a together with the channel 85a forms a supply channel mentioned in the claims, and the solution discharge pipe 88b together with the channel 85b forms a discharge channel mentioned in the claims. Further, though FIG. 10 shows, for convenience sake of illustration, a state where one of the connectors 87 and the sample solution discharge pipe 87b are attached to the cover 81, they are detachable from the cover 81 similarly to the other connector 87 and the sample solution supply pipe 87a.

Figure 13:
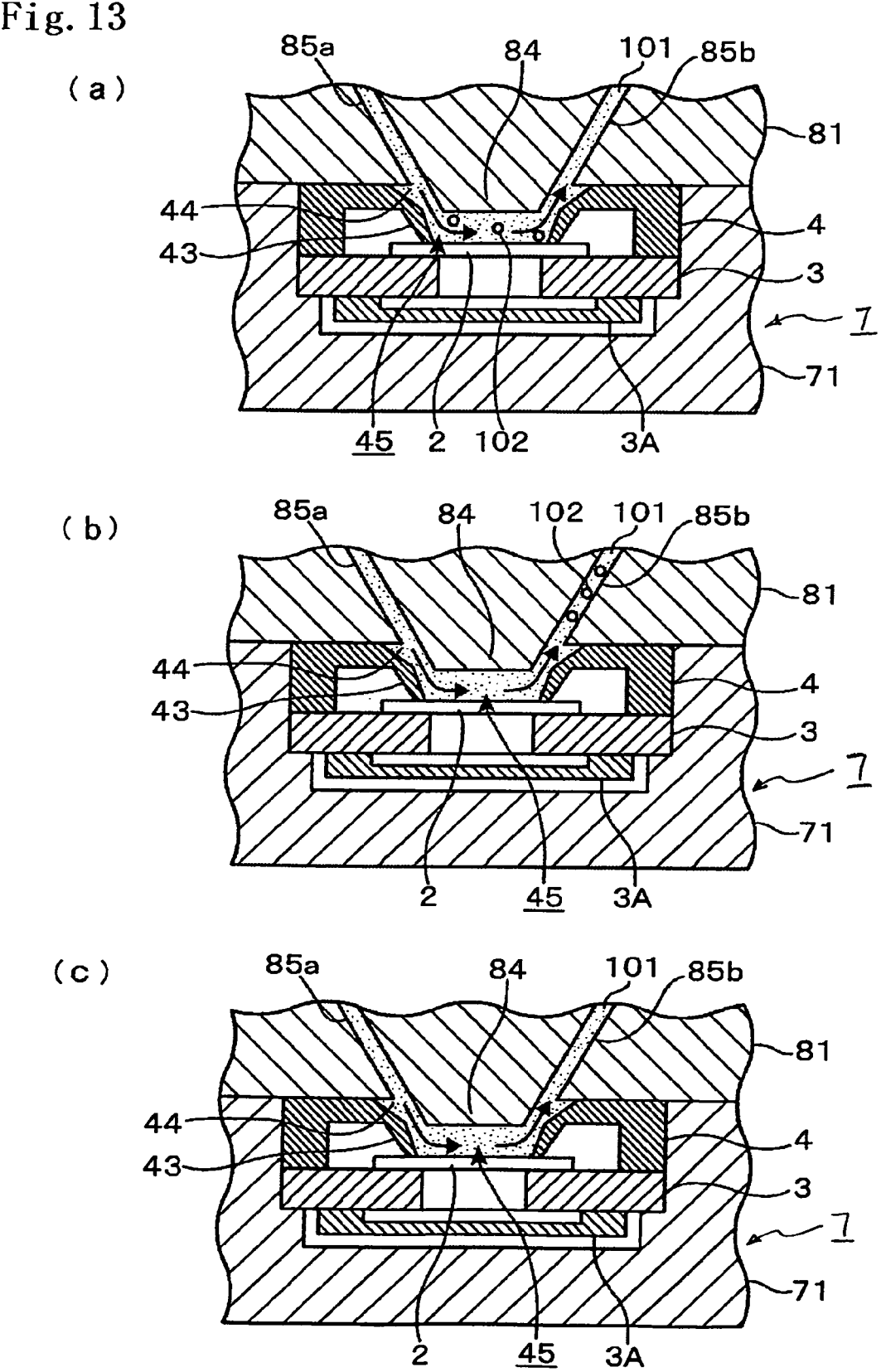
FIG. 13 are explanatory views showing states of bubbles in a sample solution stored in the quartz sensor.

As shown in FIG. 13(a), in the quartz sensor 7, upon supply of the sample solution 101 to the solution storage space 45 via the sample solution supply pipe 88a and the channel 85a, the sample solution 101 in the solution storage space 45 is sucked via the channel 85b and the sample solution discharge pipe 88b, whereby the sample solution 101 is made to flow above the excitation electrode 22 at a velocity of, for example, 50 μL/min, and a substance to be measured in the sample solution is adsorbed by the excitation electrode 22. Even if the bubbles 102 are mixed in the sample solution 101 to enter the opening portion 44 at this time, since in the corner portion made by the annular projection 43 and the quartz resonator 2, an upper side of the bubbles 102 is opened, the bubbles 102 are prevented from staying in this corner portion as shown in FIG. 13(b), (c), and thus are pushed by the sample solution 101 to easily flow into the channel 85b and are removed from the solution storage space 45. As a result, high-precision measurement is made possible as in the previously described quartz sensor 20.

Figure 14:
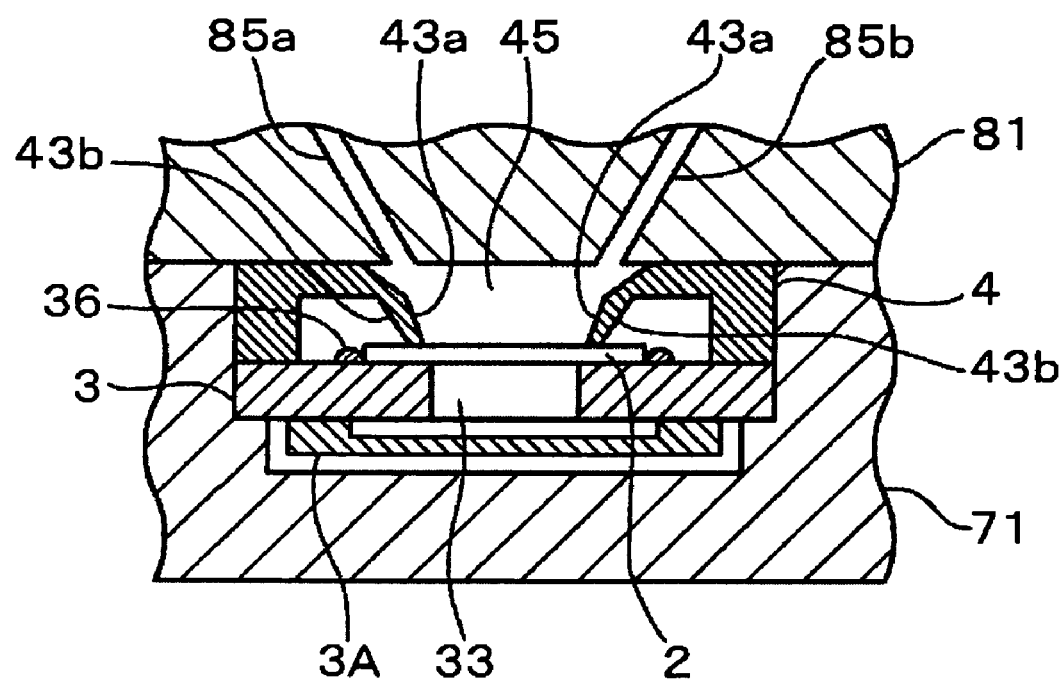
FIG. 14 is an explanatory view showing another structure of the solution supply/discharge cover.
Figure 15:
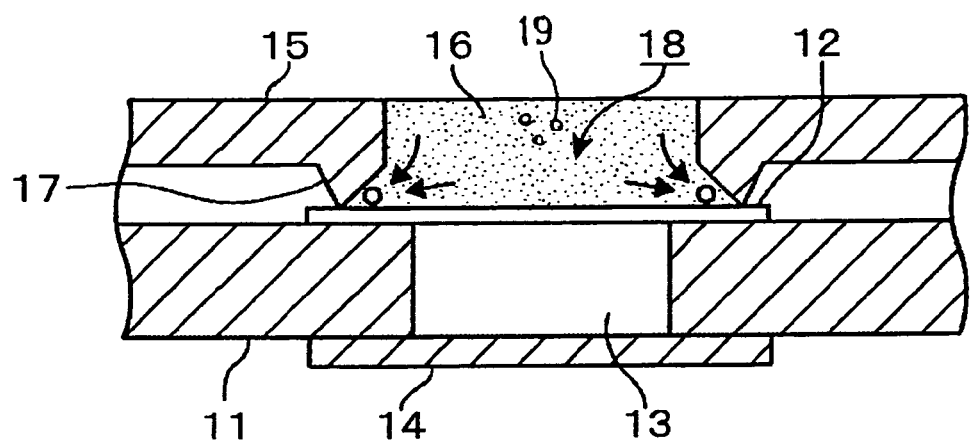
FIG. 15 is an explanatory view showing a state of bubbles in a sample solution stored in a conventional quartz sensor.

Further, since the sample solution is made to flow immediately above the excitation electrode 22 by the projection 84 as described above, adsorption of the substance to be measured by the excitation electrode 22 is increased, which enables higher-precision measurement. It should be noted that the structure without the projection 84 as shown in FIG. 14 may be adopted though the structure with the projection 84 is preferable. Moreover, the connectors 87, 87, the sample solution supply pipe 88a, and the sample solution discharge pipe 88b are attachable/detachable to/from the solution supply/discharge cover 81, and thus can be easily cleaned after the measurement by being detached from the cover, which can reduce the trouble and cost required for the cleaning, resulting in reduction in cost required for the measurement.

Further, the positions of the wiring board 3 and the quartz pressing member 4 are fixed relative to the support 71 via the engagement holes 37a, 37b, 46a, 46b provided in the wiring board 3 and the quartz pressing member 4 and via the projections 73 of the support 71, so that the misalignment of the solution storage space 45 for the sample solution relative to the solution channel 85a and the solution channel 85b of the solution supply/discharge cover 81 is prevented. Therefore, the liquid flow into the solution storage space 45 is prevented from varying at each measurement, which can prevent the occurrence of a measurement error due to the variation in the liquid flow.

In the above-described embodiments, the adsorption layer including the antibody for the substance to be measured is provided on the front surface of the excitation electrode 22 on the side, of the quartz resonator 2, facing the solution storage space 45, but the present invention is also applicable to a case where such an antibody is not provided. For example, when the measurement is conducted for research aiming at analyzing how the antibody adheres to the excitation electrode 22 of the quartz resonator 2, the measurement is sometimes conducted in such a manner that, without the antibody provided, the excitation electrode 22 physically adsorbs a substance to be measured and the substance is detected.

What is claimed is:

1. A piezoelectric sensor electrically connected to a measuring device main body in order to sense a substance to be measured in a sample solution, the piezoelectric sensor comprising:
   a wiring board which has a connection terminal portion connected to the measuring device main body and on whose one surface an electrode electrically connected to the connection terminal portion and a recessed portion forming an airtight space are provided;
   a piezoelectric resonator which includes excitation electrodes provided on one surface and on another surface of a plate-shaped piezoelectric piece respectively and electrically connected to the electrode, and which is provided on said wiring board to cover the recessed portion, with the excitation electrode on the other surface facing the recessed portion;

a pressing member in which a solution storage space having a bottom surface being the one surface of said piezoelectric resonator is formed, and which is made of an elastic material provided to surround the solution storage space; and a solution injection cover placed opposite said wiring board to cover said pressing member, and having, on a front surface thereof, an injection port which communicates with the solution storage space and through which the sample solution is injected into the solution storage space, wherein said pressing member includes an annular projection which presses a portion, of the one surface of said piezoelectric resonator, outside the recessed portion toward said wiring board to fix a position of said piezoelectric resonator;

a tip of the annular projection has an acute angle, with both side surfaces of the annular projection getting smaller in diameter toward a lower side and a distance between the both side surfaces getting smaller toward the lower side; and a natural frequency of said piezoelectric resonator changes when the substance to be measured in the sample solution stored in the solution storage space comes into contact with the one surface of said piezoelectric resonator.

2. The piezoelectric sensor according to claim 1, wherein a claw portion bending inward is provided on an edge portion of said solution injection cover and a cutout portion is provided in said wiring board respectively, and said solution injection cover is attached to said wiring board while pressing said pressing member toward said wiring board, by the claw portion catching a peripheral edge portion of said wiring board in the cutout portion owing to an inward restoring force of the claw portion.

3. The piezoelectric sensor according to claim 1, wherein the excitation electrodes of said piezoelectric resonator and the electrode of said wiring board are electrically connected to each other by the annular projection pressing said piezoelectric resonator toward said wiring board.

4. A sensing instrument comprising:
the piezoelectric sensor according to claim 1; and
the measuring device main body, wherein the measuring device main body detects a change amount of the natural frequency of said piezoelectric resonator to sense the substance to be measured in the sample solution based on the detection result.

5. A piezoelectric sensor electrically connected to a measuring device main body in order to sense a substance to be measured in a sample solution, the piezoelectric sensor comprising:

a wiring board which has a connection terminal portion connected to the measuring device main body and on whose one surface an electrode electrically connected to the connection terminal portion and a recessed portion forming an airtight space are provided;

a piezoelectric resonator which includes excitation electrodes provided on one surface and on another surface of a plate-shaped piezoelectric piece respectively and electrically connected to the electrode, and which is provided on said wiring board to cover the recessed portion, with the excitation electrode on the other surface facing the recessed portion;

a pressing member in which a solution storage space having a bottom surface being the one surface of said piezoelectric resonator is formed, and which is made of an elastic material provided to surround the solution storage space;

a support supporting said wiring board; and a solution supply/discharge cover which includes a supply channel communicating with the solution storage space to supply the sample solution into the solution storage space; and a discharge channel communicating with the solution storage space to discharge the sample solution stored in the space, and which is fixed to said support while placed opposite said wiring board to cover said pressing member, wherein said pressing member includes an annular projection which presses a portion, of the one surface of said piezoelectric resonator, outside the recessed portion toward said wiring board to fix a position of said piezoelectric resonator; a tip of the annular projection has an acute angle, with both side surfaces of the annular projection getting smaller in diameter toward a lower side and a distance between the both side surfaces getting smaller toward the lower side; and a natural frequency of said piezoelectric resonator changes when a liquid flow is formed in the solution storage space by the supply and discharge of the sample solution to bring the substance to be measured in the sample solution into contact with the one surface of said piezoelectric resonator.

6. The piezoelectric sensor according to claim 5, wherein a projection entering the solution storage space to restrict the liquid flow in an up and down direction in the solution storage space is provided in a lower portion of said solution supply/discharge cover.

7. The piezoelectric sensor according to claim 5, wherein:
holes overlapping each other are provided in said wiring board and said pressing member respectively; and
a projection corresponding to the holes is provided in said support to fix positions of said wiring board and said pressing member on said support.

8. The piezoelectric sensor according to claim 5, wherein the supply channel includes a solution supply pipe attachable/detachable to/from said solution supply/discharge cover, the discharge channel includes a solution discharge pipe attachable/detachable to/from said solution supply/discharge cover, and the solution supply pipe and the solution discharge pipe are mounted to said solution supply/discharge cover via connectors attachable/detachable to/from said solution supply/discharge cover.

9. The piezoelectric sensor according to claim 5, wherein the excitation electrodes of said piezoelectric resonator and the electrode of said wiring board are electrically connected to each other by the annular projection pressing said piezoelectric resonator toward said wiring board.

10. A sensing instrument comprising:
the piezoelectric sensor according to claim 5; and
the measuring device main body, wherein the measuring device main body detects a change amount of a natural frequency of said piezoelectric resonator to sense an substance to be measured in a sample solution based on the detection result.

* * * * *